(12) United States Patent
Stehr et al.

(10) Patent No.: US 8,182,466 B2
(45) Date of Patent: May 22, 2012

(54) DUAL BRAIDED CATHETER SHAFT

(75) Inventors: Richard E. Stehr, Stillwater, MN (US); Troy T. Tegg, Elk River, MN (US); Michael J. Johnson, Minneapolis, MN (US); Allan M. Fuentes, Mound, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 0 days.

(21) Appl. No.: 11/618,570

(22) Filed: Dec. 29, 2006

(65) Prior Publication Data

US 2008/0161762 A1    Jul. 3, 2008

(51) Int. Cl.
*A61M 25/00* (2006.01)
(52) U.S. Cl. ......... 604/525; 604/524; 604/526; 604/527
(58) Field of Classification Search .................. 604/523, 604/524–527
See application file for complete search history.

(56) References Cited

U.S. PATENT DOCUMENTS

| | | | |
|---|---|---|---|
| 4,817,613 A | | 4/1989 | Jaraczewshi et al. |
| 4,981,478 A | * | 1/1991 | Evard et al. .................. 604/527 |
| 5,554,139 A | * | 9/1996 | Okajima ........................ 604/526 |
| 5,755,704 A | | 5/1998 | Lunn |
| 5,853,400 A | * | 12/1998 | Samson ........................ 604/526 |
| 5,873,866 A | | 2/1999 | Kondo et al. |
| 6,143,013 A | * | 11/2000 | Samson et al. ................ 606/192 |
| 6,702,782 B2 | * | 3/2004 | Miller et al. ................ 604/96.01 |
| 6,945,970 B2 | * | 9/2005 | Pepin ............................ 604/525 |
| 2003/0191451 A1 | | 10/2003 | Gilmartin |
| 2004/0176740 A1 | * | 9/2004 | Chouinard ................... 604/527 |
| 2005/0061771 A1 | * | 3/2005 | Murphy ........................ 216/17 |
| 2006/0030835 A1 | * | 2/2006 | Sherman et al. ............. 604/526 |

OTHER PUBLICATIONS

"Supplementary European Search Report", EP Application No. 07 865 983.6 Feb. 28, 2011, (6 pages).

* cited by examiner

*Primary Examiner* — Bhisma Mehta
(74) *Attorney, Agent, or Firm* — Marsh Fischmann & Breyfogle LLP

(57) ABSTRACT

A dual braided catheter shaft includes a flat wire forming the inner braid, thereby potentially allowing for reduced radial thickness of the shaft. In one embodiment, the shaft (100) includes an inner polymer jacket (104), an inner braid (106) formed on the inner jacket (104), an intermediate jacket (108) formed over the inner braid (106), an outer braid (110) formed on the intermediate jacket (108) and an outer jacket (112) formed on the outer braid (110). A preferred construction process involves extruding polymer material directly onto each of the inner and outer braids (106 and 110) so that little or no air gaps remain between the polymer material and the braids (106 and 110). The braiding parameters of the inner and outer braids (106 and 110) can be varied along the length of the catheter to provide varying mechanical properties.

24 Claims, 10 Drawing Sheets

DUAL BRAIDED CATHETER SHAFT

BACKGROUND OF THE INVENTION a. Field of the Invention

The present invention relates generally to catheter shafts and, in particular, to a dual braided shaft with a reduced thickness that can be constructed with reduced reflowing of polymers.

b. Background Art

Catheters are typically threaded through a blood vessel of a patient to reach a desired site for a medical procedure. For example, in the diagnosis and treatment of atrial fibrillation, a catheter may be routed through a vessel from a patient's leg or neck to access chambers of a patient's heart. Electrodes at the distal end of the catheter can then be used for a variety of purposes including electrical mapping and ablation. The catheter therefore may include one or more internal lumens to accommodate electrode wiring and steering wires, as well as to permit irrigation as may be useful for certain procedures.

The catheter body or shaft is therefore designed with a number of objectives in mind. First, the shaft is generally dimensioned with an outside diameter that allows the catheter to be threaded through the vessels necessary to perform the desired medical procedures. In addition, it is desired to provide an inside diameter sufficient to accommodate electrode wiring, steering wiring and/or irrigation fluid channels, depending on the intended use of the catheter. Therefore, a limited radial thickness is desirable.

At the same time, the shaft should provide certain mechanical properties for optimal functioning. In particular, the shaft should resist compression during use and transmit torque. With regard to resisting compression, it is important for the physician to be able to advance the catheter through the vessel, sometimes against significant frictional resistance, without undue axial compression or snaking of the catheter shaft. Such compression can complicate positioning of the distal end of the catheter at the desired location for a medical procedure. In addition, skilled physicians often rely, to some extent, on tactile feedback to attain and verify proper positioning of the catheter, and such feedback can be impaired by excessive compressibility.

The shaft should also be capable of reliably transmitting torque. In this regard, a physician normally navigates the distal end of the catheter to a desired location in part by turning a handle set at the proximal end of the catheter. Again, substantial frictional forces sometimes resist transmission of torque across the length of the catheter. In some cases, these forces can cause the shaft to twist about a longitudinal axis of the shaft, storing energy in the process in spring-like fashion. If this energy is released suddenly, the distal end of the catheter, which may be bent by a steering mechanism, can be propelled with significant force against unintended tissue. This can have dire consequences in the context of intracardiac procedures.

In order to provide the desired mechanical properties within the noted dimensional constraints, some catheters incorporate a dual braided shaft design involving an inner braided wire and an outer braided wire. Each of braided wires is typically embedded, to some extent, in a polymer so that the braided wire and polymer function as a system to impart desired mechanical properties. More specifically, the inner braided wire system is typically the primary source of compression resistance. The outer braided wire system, having a larger moment arm relative to the longitudinal axis of the shaft, is typically the principal source of torque transmission. Each of the inner and outer braided wire systems may be designed to satisfy its primary function in this regard.

The dual braided shaft is generally formed by extruding a polymer liner on a rod. The outer braid is then formed on the polymer liner, and an outer polymer jacket is then extruded onto the outer braid. Thereafter, the rod is removed to leave a hollow interior. A coil is then inserted into the hollow interior to form the inner braid, and the polymer liner is reflowed along the length of the shaft to integrate, to some extent, the inner braid into the catheter shaft structure.

BRIEF SUMMARY OF THE INVENTION

It has been recognized that there are a number of disadvantages associated with this dual braided catheter construction process and the resulting product. First, the coil inserted into the hollow interior to form the inner braid is generally wound with round wire to be self supporting prior to integration into the shaft structure. This limits the designer's ability to optimize the inner coil design and, specifically, tends to reduce the inner diameter of the shaft, thereby reducing the size of the lumen that is available for wiring, irrigation and the like. In addition, as noted above, it is generally necessary to reflow the polymer liner along the length of the shaft to get the coil to adhere to, and become integrated with, the shaft structure. This increases the difficulty of construction and associated costs. Moreover, the reflow process may not result in the inner braid being fully embedded in the polymer. That is, small air pockets may remain between the coil and the polymer, which can adversely affect the mechanical properties of the coil/polymer system.

Using the conventional processes, it is also difficult to construct a catheter shaft having varying properties along its length. In this regard, it may be desirable to vary the mechanical properties along the length of the catheter, for example, to provide greater compression resistance at one section of the shaft (e.g., towards the proximate end of the catheter) and greater flexibility at another section (e.g., towards the distal end). In conventional processes, the coil properties are constant along the length of the catheter and any variation in the mechanical properties of the shaft along the length thereof in relation to the inner braid system are achieved by varying the durometer of the polymer. However, it is generally impractical to attempt to vary the material extruded in a continuous process to the desired accuracy. Instead, coils are extruded with different materials, and then segments of the coils with different extruded materials are fitted together piecewise to form a catheter shaft with varying properties along its length. However, because the shaft is not formed in a continuous flow process, such construction is slow and expensive.

The present invention overcomes a number of disadvantages associated with conventional catheter shaft construction processes to provide an improved construction process and catheter shaft. In particular, the present invention allows for use of flat wires for the inner braid of a dual braided shaft, thereby enhancing design flexibility and allowing for potentially reduced radial thickness, e.g., for reduced shaft outside diameter and/or increased shaft inside diameter. Moreover, a dual braided shaft can be formed in accordance with the present invention with reduced reflowing of polymers, thus reducing construction complexity and costs. Moreover, a dual braided shaft can be formed in a series of extrusion and braiding processes so as to minimize the occurrence of air pockets in the finished shaft. The invention also enables variation of the mechanical properties of the shaft along the length thereof in relation to the inner braid system in a continuous flow process.

In accordance with one aspect of the present invention, a dual braided catheter shaft includes an inner braid formed from a flat wire. Specifically, the catheter shaft includes a first wire wound to form an inner cylindrical braid structure and a second wire wound to form an outer cylindrical braid structure where the inner braid structure is disposed substantially inside of the outer braid structure, e.g., the braid structures may be substantially coaxial. The catheter shaft further includes an intermediate polymer material disposed at least between the inner cylindrical braid structure and the outer cylindrical braid structure. The first wire that forms the inner braid structure is a flat wire having a minor cross-sectional dimension and a major cross-sectional dimension, where the major dimension is greater than the minor dimension. For example, the first wire may have an elliptical, a rectangular or other noncircular cross-section. The first wire is preferably oriented such that the major dimension is substantially aligned with a longitudinal axis of the inner braid structure and the minor axis is substantially aligned with a radial axis of the braid structure. This allows for a smaller overall radial dimension of the catheter shaft, which may be reflected in a smaller outside diameter and/or a greater inside diameter of the catheter shaft.

In accordance with another aspect of the present invention, a dual braided shaft is formed as a series of polymer layers and braid structures. In this regard, the apparatus includes a first cylindrical layer of polymer material defining at least one internal lumen, a first wire wound to form an inner cylindrical braid structure substantially on an outer surface of the first layer, a second cylindrical layer of polymer material substantially on the outside of the inner cylindrical braid structure, and a second wire wound to form an outer cylindrical braid structure substantially on the outer surface of the second layer. A further outer cylindrical layer of polymer may be provided substantially on the outside of the second wire. The catheter shaft thereby defines an integral laminar structure for potentially improved mechanical characteristics. Additionally, the mechanical properties of the shaft can be varied along the length thereof by varying the braiding parameters of the inner and/or outer braid structure in a continuous flow process.

In accordance with a still further aspect of the present invention, a method is provided for constructing a catheter shaft that allows for improved integration of the inner braid into a dual braided shaft structure. The dual braided shaft structure includes an inner braid and an outer braid outside of the inner braid. The noted construction method includes the steps of braiding a first wire to form the inner braid and extruding a melt processable polymer over the braided first wire. For example, a braiding machine may be used to braid the first wire on a rod, e.g., directly on the rod or on a polymer layer previously extruded onto the rod. Thereafter, the melt processable polymer may be extruded onto the first wire such that the first wire is embedded in the polymer with little or no air gaps therebetween. In this manner, an inner braid system including the first wire and the polymer has potentially improved mechanical properties. In addition, a flat wire can be used to form the inner braid, as it is not necessary for the first wire to be self-supporting prior to extrusion of the polymer over the wire.

In accordance with a still further aspect of the present invention, a method for use in constructing a catheter shaft involves the serial application of a number of layers to form a dual braided shaft. Specifically, the method includes the steps of forming a first cylindrical layer of polymer material, braiding a first wire on a first outside surface of the first cylindrical layer, forming a second cylindrical layer of polymer material over the braided first wire, and braiding a second wire on a second outside surface of the second cylindrical layer. An additional outer layer of polymer material may then be formed on the braided second wire. It will be appreciated that the dual braided shaft can thereby be formed in a continuous process to define an integral system with potentially improved mechanical properties. Moreover, the mechanical properties of the shaft can be varied along the length of the shaft by changing the braiding parameters when braiding the first and/or second wires. Thus, a dual braided shaft with variable properties along the length thereof can be formed in a continuous flow process, thereby reducing construction complexity and cost.

The foregoing and other aspects, features, details, utilities, and advantages of the present invention will be apparent from reading the following description and claims, and from reviewing the accompanying drawings.

DETAILED DESCRIPTION OF THE INVENTION

In the following description, the invention is set forth in the context of certain examples of a dual braided catheter shaft and associated construction processes. While these examples illustrate certain advantageous implementations of the present invention, the invention is not limited to the specific examples described below. Accordingly, the following description should be understood as exemplifying the invention and not by way of limitation.

Figure 4:
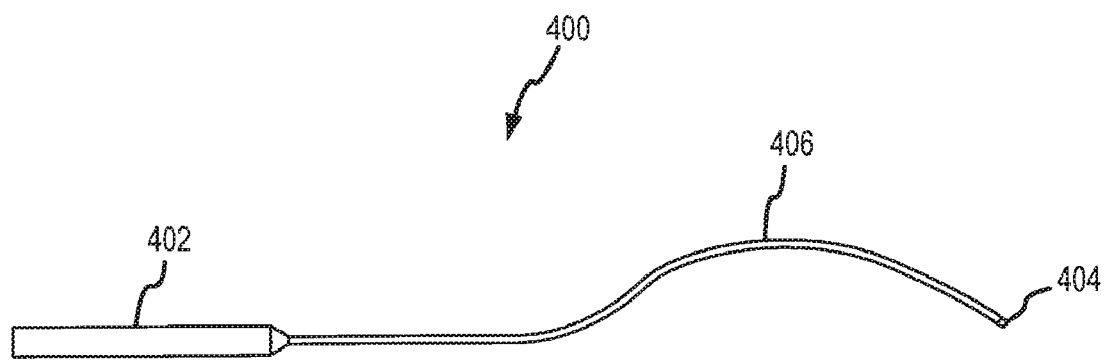
FIG. 4 shows an electrode catheter including a catheter shaft constructed in accordance with the present invention.

FIG. 4 shows and electrode catheter 400 that may employ a catheter shaft 406 constructed in accordance with the present invention. Generally, the catheter 400 includes a handle set 402, an electrode tip 404 and the catheter shaft 406 that extends between the handle set 402, at the proximal end of the catheter shaft 406, and the electrode tip 404 at the distal end of the catheter shaft. The catheter 400 may include other components such as steering mechanisms, irrigation components and the like that are omitted from the drawing for the sake of simplicity.

The catheter is used to position the electrode tip 404 at a desired location for a medical procedure, e.g., in the case of diagnosing or treating atrial fibrillation, the catheter tip 404 may be positioned against an internal wall of the patient's heart. This location may be accessed, for example, by threading the shaft 406 through a blood vessel of the patient from a location in the patient's leg or neck. It will be appreciated that a variety of different types of electrode assemblies may be used in connection with the catheter 400 depending on the specific application involved. For example, one or more ablation and/or mapping electrodes may be disposed at the distal end of the catheter shaft 406. Accordingly, the illustration of a particular electrode tip 404 is not intended to imply any limitation in this regard.

In use, the physician manipulates the handle set 402 to advance, withdraw, rotate and otherwise position the electrode tip 404 at a desired location. It will be appreciated that significant frictional resistance may sometimes be experienced in connection with such manipulation. In addition, experienced physicians rely to some extent on tactile feedback, transmitted back from the electrode tip 404 to the handle set 402 via the shaft 406, in identifying a proper electrode position for a procedure. It is therefore desirable for the shaft 406 to be sufficiently incompressible and have sufficient torsional rigidity to allow such manipulation without substantial compression or twisting and to reliably provide the tactile feedback that is useful to physicians. The discussion below describes a suitable shaft in this regard as well as associated construction techniques.

Figure 1A:
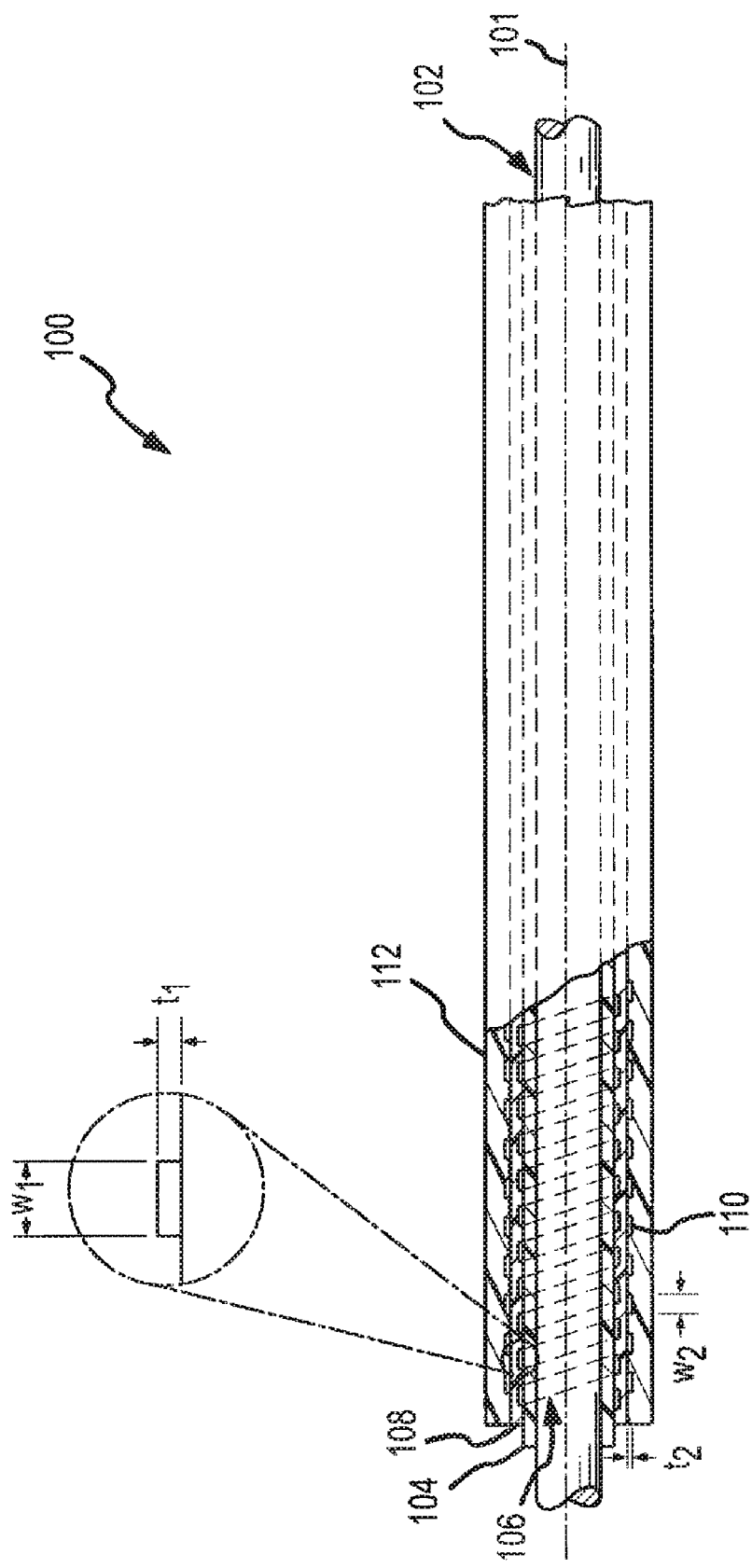
FIG. 1A is a side cross-sectional view of a dual braided catheter shaft in accordance with the present invention.
Figure 1B:
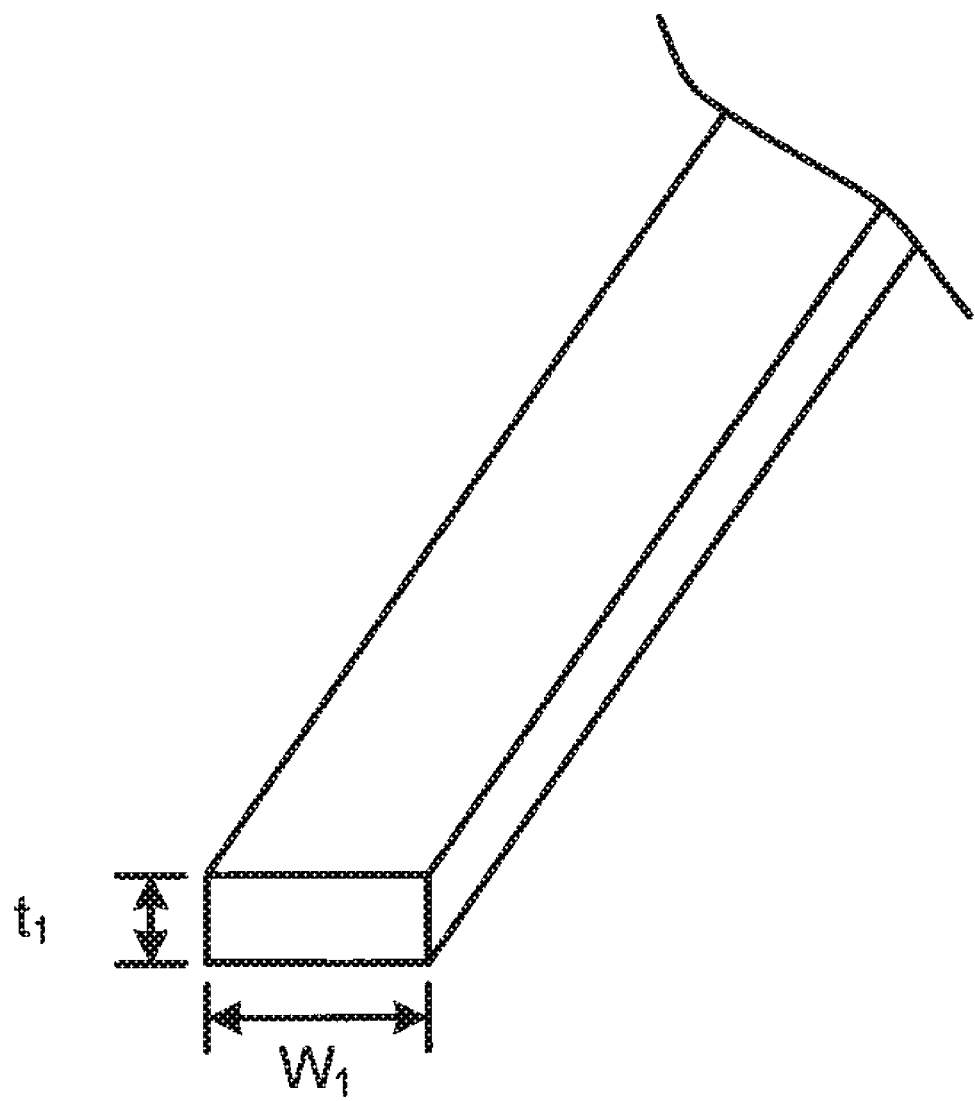
FIG. 1B is a perspective view of a wire used to form a braid of the shaft of FIG. 1A.

Referring to FIG. 1, a side, partially cross-sectional view of a dual braided catheter shaft 100 in accordance with the present invention is shown. FIG. 1A also shows a core rod 102 used during construction of the shaft 100. The rod 102 is removed after construction and is not a part of the shaft 100. Rather, a central lumen remains after the rod 102 is withdrawn. This lumen may be used for a variety of purposes, including wiring for electrodes, steering wires, irrigation fluid passageways and the like. It will be appreciated that multiple lumens may be provided in the area vacated by the rod 102. Alternatively, the shaft 100 may be constructed on a hollow rod that remains as part of the shaft 100. The hollow rod defines a hollow interior for passage of irrigation fluids or wires. The hollow rod may also include a number of longitudinal channels, e.g., formed on the external surface thereof, for routing of electrode wires, steering wires and the like. The various layers of the illustrated shaft 100 can then be formed on the hollow rod.

The illustrated shaft 100 is formed from a number of layers of material sequentially formed on the core rod 102. These layers include an inner jacket 104 formed on the rod 102, an inner braid 106 formed on the inner jacket 104, an intermediate jacket 108 formed over the inner braid 106, an outer braid 110 formed on the intermediate jacket 108 and an outer jacket 112 formed over the outer braid 110. These layers 104, 106, 108, 110 and 112 thus form an integral catheter shaft system with minimal, if any, air pockets between the layers.

The inner jacket 104 is formed from a melt processable polymer extruded directly onto the rod 102. For example, the inner jacket 104 may be formed from any of various polymers having a durometer selected to impart desired mechanical properties to the shaft 100, as will be described in more detail below. Suitable polymers include those well known in the art, such as polyurethanes, polyether-block amides, polyolefins, nylons, polytetrafluoroethylene, polyvinylidene fluoride and fluorinated ethylene propylene polymers, and other materials. A braiding machine can then be operated to wind a wire around the inner jacket 104 so as to form the inner braid 106. For example, the inner braid 106 may be constructed by winding a flat wire formed from any of various metals such as stainless steel.

The second jacket 108 is formed from a melt processable polymer (example set forth above) and can be extruded over the inner jacket 104 and inner braid 106. In this manner, the inner braid 106 is embedded in the intermediate jacket 108 with few or substantially no air pockets for potentially improved mechanical characteristics, i.e., the intermediate jacket 108 extends between successive windings of said inner braid 106 so as to contact opposite facing surfaces of the windings. The material used for the intermediate jacket 108 can be the same as or different than the inner jacket 104, and it can have the same or a different durometer.

After the intermediate jacket 108 has been formed, a braiding machine can be operated to wind a wire on the intermediate jacket 108 to form the outer braid 110. For example, a flat wire formed from metal such as stainless steel can be used in constructing the outer braid 110. The material of the wire used to form the outer braid 110 can be the same as or different than the material used to form the wire of the inner braid 106. In addition, the dimensions and winding parameters of the outer braid 110 can be the same as or different than those for the inner braid 106. Some considerations in this regard will be discussed in more detail below.

After the outer braid 110 has been applied, the outer jacket 112 is formed on the intermediate jacket 108 and outer braid 110. For example, the outer jacket 112 may be formed from a melt processable polymer (examples set forth above) and may be extruded directly onto the intermediate jacket 108 and outer braid 110. In this manner, the outer braid 110 is substantially fully embedded in the outer jacket 112 with few or substantially no air pockets therebetween for potentially enhanced mechanical properties. The outer jacket 112 may be formed from the same material as the intermediate jacket 108 and/or inner jacket 104 or different materials may be used. In addition, the outer jacket 112 may have the same or a different durometer than the intermediate jacket 108 and/or inner jacket 104.

The properties of the various layers 104, 106, 108, 110 and 112 can be selected to impart desired properties to the completed shaft 100. In this regard, it is generally desirable that the shaft 100 be substantially incompressible. In addition, it is generally desired that the shaft 100 effectively transmit torque across the length of the shaft so that a torque applied by a physician on the handle set at the proximate end of the shaft is effectively transmitted to an electrode or other tool at the distal end of the shaft. That is, the shaft should resist twisting about the longitudinal axis 101 of the shaft 100 in the event of significant frictional resistance to such torque. On the other hand, it is generally desired that the shaft 100 (including a dual braided body section defined by the inner braid 106, intermediate jacket 108 and outer braid 110) be sufficiently flexible to allow for threading through a blood vessel of a patient and steering of the distal end of the catheter to a desired location for a medical procedure. The mechanical properties of the shaft 100 may vary along a length of the shaft in this regard, i.e., the dual braided body section may have a first value of a mechanical property at a first portion and a second value, different from the first value, at a second portion thereof.

It will be appreciated that any and all of the layers 104, 106, 108, 110 and 112 may be involved in providing the desired properties. However, in the illustrated embodiment, the inner braid system provides the primary axial rigidity for the desired incompressibility (e.g., a first mechanical property of the catheter), and the outer braid system, which has a greater moment arm in relation to the axis 101, provides the primary torsionally rigidity for transmitting torque (e.g., a second mechanical property of the catheter). As previously noted, the parameters of these braids may be altered independently along the length or longitudinal section of the catheter to vary the properties of the catheter. The inner braid system includes the inner braid 106 and the intermediate jacket 108 that is extruded onto the inner braid 106. These components cooperate to provide a desired level of axial rigidity. That is, these components may cooperate to provide a first mechanical property to the catheter. Thus, the axial rigidity of the inner braid system is principally determined by the durometer of the intermediate jacket material, the material and dimensions of the wire used to form the inner braid 106, and the braiding parameters including the pic rate (number of windings per inch) of the inner braid 106. That is, a first mechanical property of the catheter may be a function of the dimensions of the first wire and/or material properties of the polymer. With regard to the material used to form the intermediate jacket 108, the higher the durometer of this material, the greater the axial rigidity of the inner braid system, all other factors being equal. Again, it is noted that a catheter designer may balance the need for shaft flexibility with the desire for axial rigidity.

With regard to the material used to form the inner braid 106, generally, the harder the material the greater the axial rigidity. The axial rigidity can also be enhanced by increasing the width $w_1$ (the axial dimension) of the wire used to form the inner braid 106 and increasing the pic rate of the inner braid 106. However, it is desirable that the thickness $t_1$ (the radial dimension) of the wire used to form the inner braid 106 should be minimized to as to reduce the overall thickness of the shaft 100. Accordingly, using a flat wire where the width $w_1$ is greater than the thickness $t_1$ (see also FIG. 1B) allows for obtaining the desired axial rigidity without unduly increasing the thickness of the shaft 100. In the illustrated example, the thickness $t_1$ may be between about 0.0005-0.004 inches, and the width $w_1$ may be between about 0.002-0.016 inches, depending on the particular catheter application. Additionally, as will be discussed in more detail below, the pic rate may be varied along the length of the catheter, for example, to provide greater flexibility near the distal end of the catheter and greater axial rigidity towards the proximate end of the catheter. For example, depending on the application, the pic rate of the inner braid 104 may be between about 25-70 pics per inch (PPI), and this value may vary along the length of the shaft 100.

Similarly, the mechanical properties (e.g., second mechanical propertied imparted to the shaft 100 by the outer braid system are principally a function of the durometer of the outer jacket material, the dimension (e.g., t2 and w2) of the outer braid wire, and the braiding parameters of the outer braid including its pic rate (which may vary along the length or longitudinal section of the shaft). Although the outer braid 110 is shown as being formed from a flat wire, a round wire or other configuration may be employed. In this regard, it is noted that a primary function of the outer wire is to impart torsional rigidity, and a greater thickness t2 may be desired within the constraints of the desired overall shaft thickness. In the illustrated embodiment, the outer braid wire has a thickness t2 of between about 0.0005-0.004 inches, a width t2 of between about 0.002-0.016 inches, and the outer braid has a pic rate of between about 30-60 PPI.

The resulting shaft 100 provides the desired incompressibility and torsional rigidity properties within a reduced thickness envelope, thereby allowing for a reduced shaft outside diameter and/or an increased shaft inside diameter. In this regard, the outside shaft diameter may be no more than about 5-7 french. The inside diameter may be at least about 3 french, and the shaft wall thickness (the outside diameter less the inside diameter) may be about 0.008 inches.

Figure 2A:
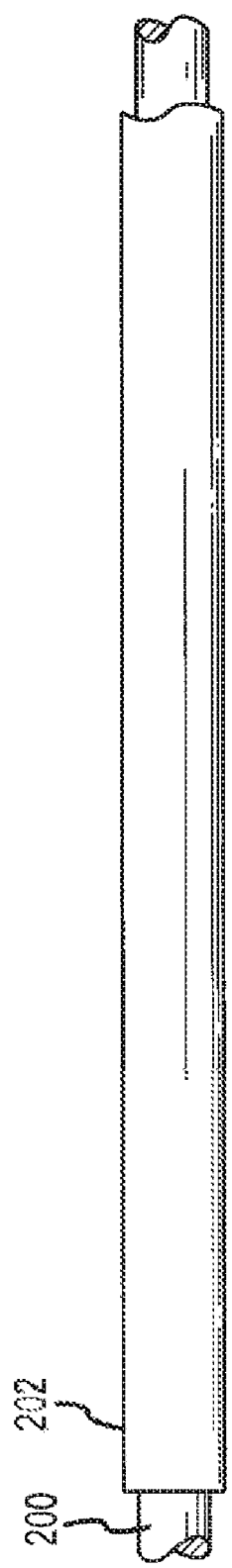
FIGS. 2A-2F illustrate a process for constructing a dual braided shaft in accordance with the present invention.
Figure 2B:
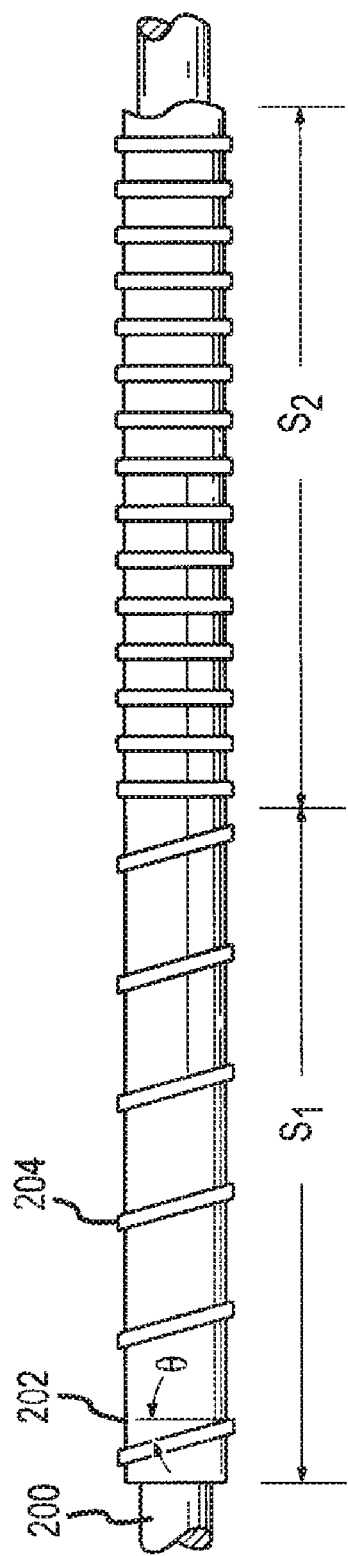

FIGS. 2A-2F graphically depict a sequence for constructing a dual braided catheter shaft 212 in accordance with the present invention. As shown in FIG. 2A, the process is initiated by extruding a melt processable polymer onto the core shaft 200 to form an inner jacket 202. Thereafter, a braiding machine is operated to braid a wire onto the inner jacket 202 to form the inner braid 204. As shown in FIG. 2B, it is possible to control the operation of the braiding machine to provide a first pic rate in a first section $s_1$ of the catheter and a second pic rate in a second section $s_2$ of the catheter. In this case, a lower pic rate is used in section $s_1$ than in section $s_2$. For example, this may be done to provide greater flexibility at a distal end of the catheter and a greater axial rigidity at a proximate end.

In this regard, the greater density of wire coverage in section $s_2$ provides a higher axial rigidity whereas the lesser density of wire coverage in section $s_2$ and the greater winding angle θ provides greater flexibility in section $s_1$.

Figure 2C:
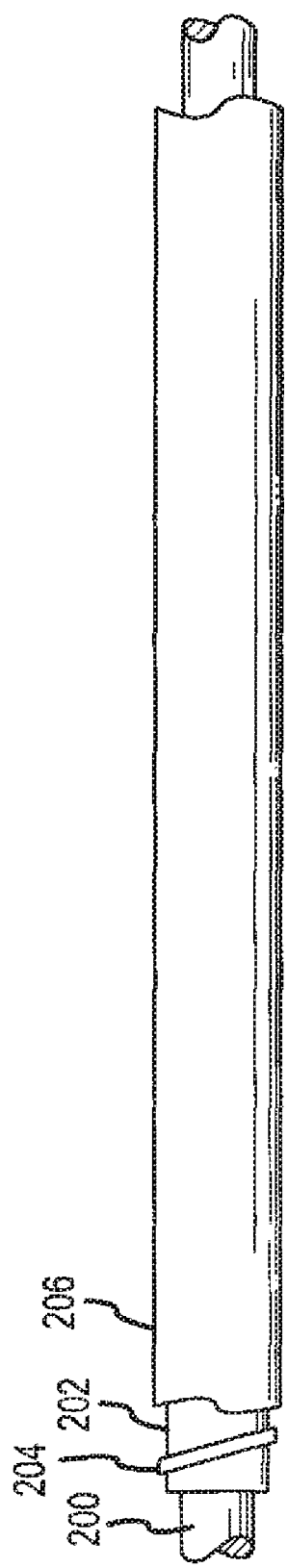
Figure 2D:
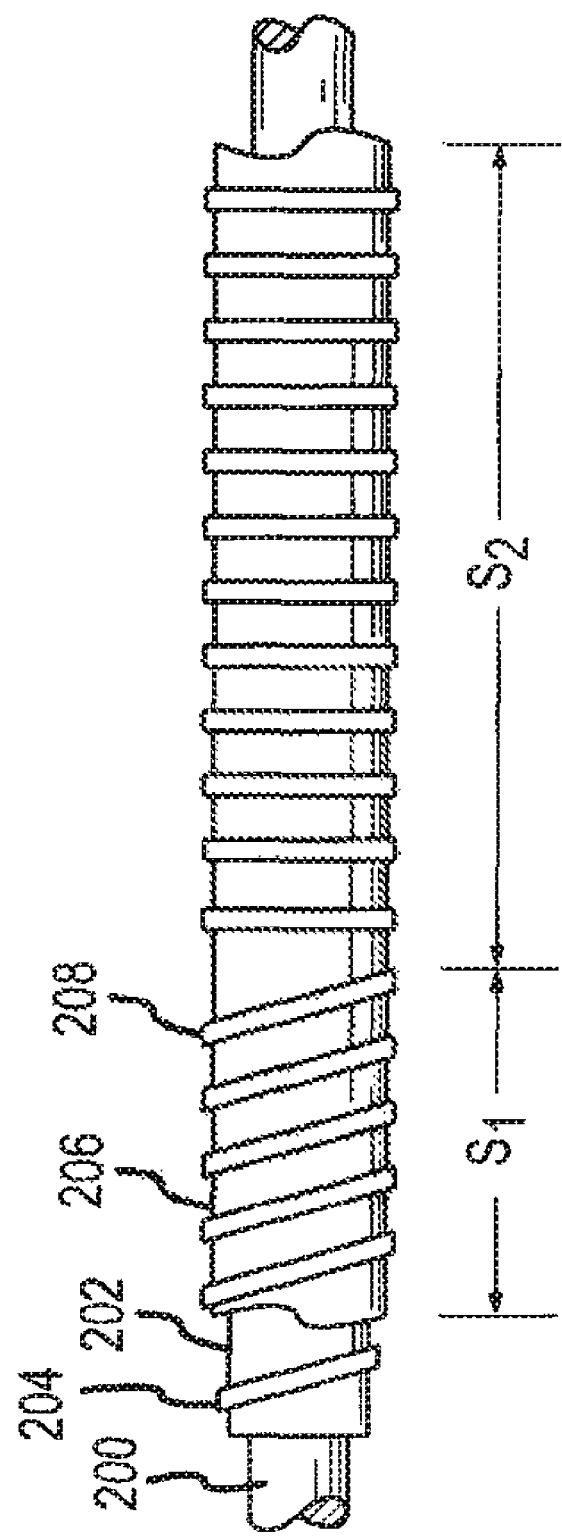

After the inner braid 204 has been formed, the intermediate jacket 206 is extruded onto the inner braid 204 and the inner jacket 202, as shown in FIG. 2C. A braiding machine can then be operated to wind a wire on the intermediate jacket 206 to form the outer braid 208, as shown in FIG. 12D. It will be appreciated that the pic rate of the outer braid 208 can also be varied along the length of the catheter to balance the desire for torsional rigidity with desire for flexibility. In addition, although the inner and outer braids 204 and 208 are shown as being wound in the same rotational sense in FIG. 2D, the braids 204 and 208 may be wound in opposite rotational senses, for example, to provide desired mechanical properties to the shaft 212.

Figure 2E:
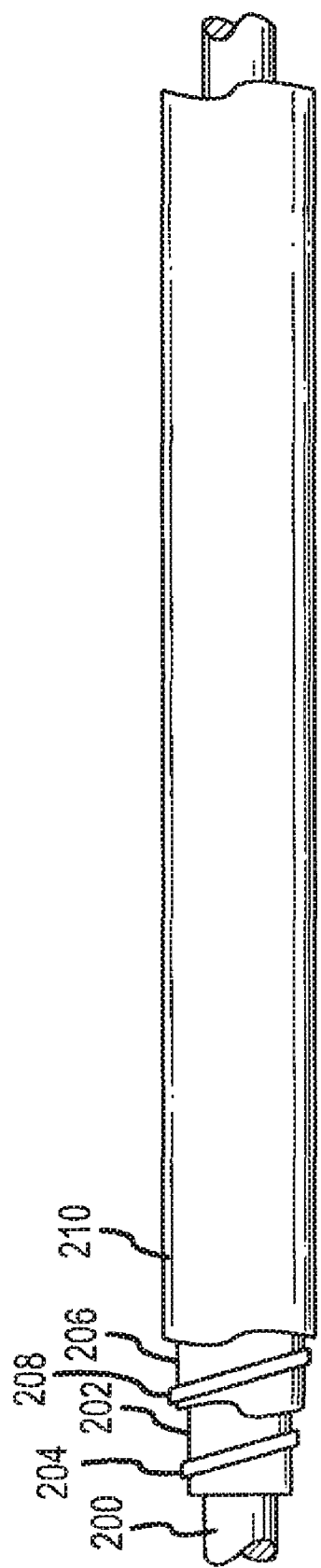
Figure 2F:
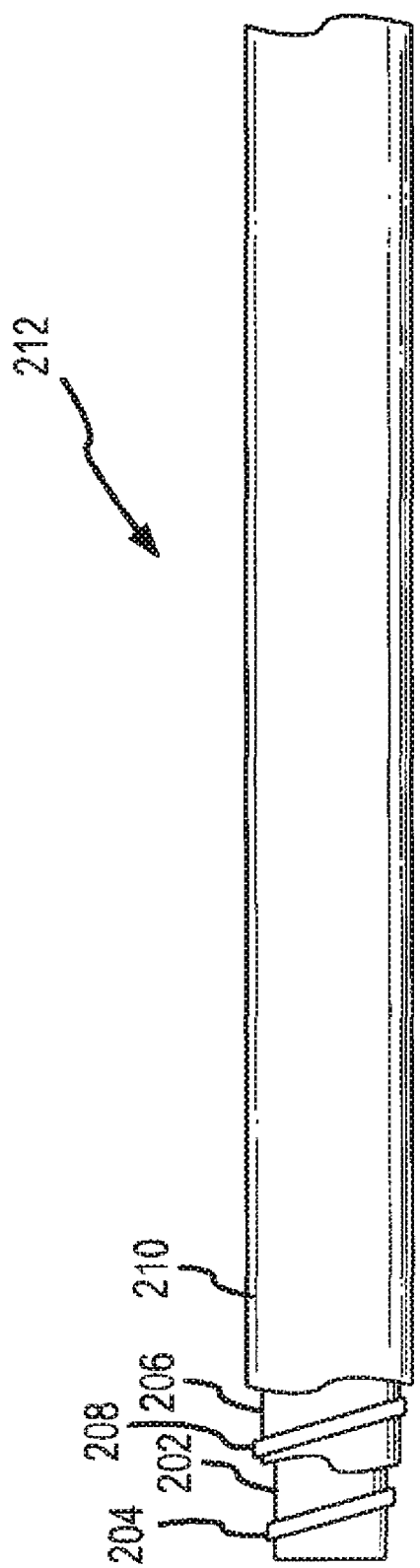

After the outer braid 208 has been formed, an outer jacket 210 is formed over the outer braid 208 and intermediate jacket 206 by extruding melt processable polymer material thereon, as shown in FIG. 2E. Finally, the core rod 200 is extracted from the assembly to form the catheter shaft 212, as shown in FIG. 2F.

Figure 3:
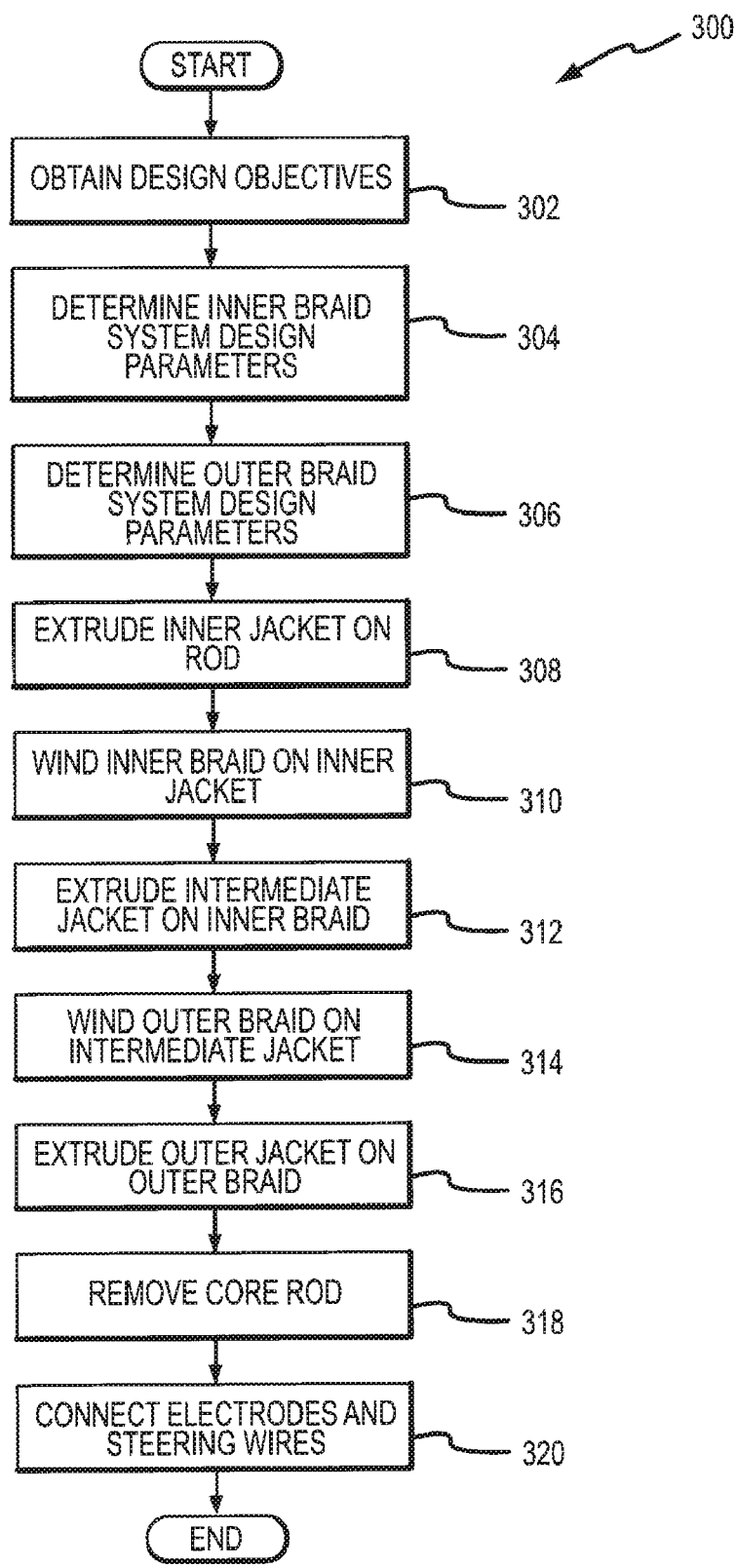
FIG. 3 is a flowchart illustrating a process for constructing a dual braided shaft in accordance with the present invention.

The overall process for designing and constructing a catheter shaft can be summarized by reference to the flowchart of FIG. 3. The illustrative process 300 is initiated by obtaining (302) design objectives for the catheter shaft. In this regard, different shaft platforms may be used for different catheter applications such as fixed curve catheters, steerable catheters, bi-directional catheters and the like. For example, the particular catheter application may dictate the need for greater flexibility or greater torsional rigidity, or may dictate a particular need for axial rigidity. In addition, the catheter application may dictate a particular limit on the outside diameter of the catheter or require an inside diameter sufficient for electrode wiring, steering wires and irrigation fluid channels. All of these objectives may be considered in relation to the design of the catheter shaft.

The designer can then determine (304) the inner braid system design parameters and determine (306) the outer braid system parameters. As noted above, the inner braid system may be used primarily to address considerations related to axial rigidity. In this regard, the duromater of the intermediate jacket material, the material used for the inner braid wire, the dimensions of the inner braid wire and the braiding parameters for the inner braid may be selected in relation to the desire for axial rigidity, on the one hand, versus catheter flexibility on the other. As illustrated above, these characteristics may vary along the length of the catheter. While it is theoretically possible to change the durometer of the intermediate jacket material along the length of catheter, as a practical matter, existing extrusion processes generally do not provide sufficient accuracy in this regard. Accordingly, in accordance with the present invention, the pic rate of the inner braid can be controlled to allow for variation of mechanical properties along the catheter shaft in a continuous flow process. This greatly increases production rates in relation to certain existing processes for varying mechanical properties by combining shaft segments in a piecewise fashion. In this regard, it is anticipated that production rates on the order of 30 feet per minute may be achieved in accordance with the present invention versus existing production rates on the order of inches per minute using existing processes.

Similarly, the outer braid system design parameters can be determined (306) in relation to the durometer of the outer jacket, the material used for the wire of the outer braid, the dimensions of the wire for the outer braid and the braiding parameters used in braiding the outer braid. These parameters may be selected to balance the desire for torsional rigidity with the desire for shaft flexibility.

After the design parameters have been determined, construction of the shaft begins by extruding (308) the inner jacket on the core rod. A braiding machine is then operating to wind or cross-braid (310) the inner braid on the inner jacket. The intermediate jacket is then formed by extruding (312) material on the inner braid an inner jacket. A braiding machine can then be again operated to wind or cross-braid (314) the outer braid on the intermediate jacket. Finally, the outer jacket is extruded (316) on the outer braid and intermediate jacket, and the core rod is removed (318) to form the catheter shaft.

Electrodes and steering wires can then be connected (320) to form the finished catheter product. The nature of these connections and additional processes will depend on the particular catheter application. For example, steering wires may be threaded through the central lumen of the catheter shaft in the case of a steerable catheter application. In addition, wiring for a single electrode or multiple electrodes may be threaded through the central lumen, depending on the application. Additional processes may be performed to define a passageway for irrigation fluid to support irrigated medical procedures. Additional reflowing steps may be required to adhere the distal catheter tip to the distal end of the catheter shaft after the electrode connections have been formed. It will be appreciated that a number of other conventional finishing processes may be implemented in this regard.

Although a number of embodiments of this invention have been described above with a certain degree of particularity, those skilled in the art could make numerous alterations to the disclosed embodiments without departing from the spirit or scope of this invention. All directional references (e.g., upper, lower, upward, downward, outer, inner, axial, radial, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A catheter apparatus, comprising:
    a proximal handle set;
    a distal tip;
    a shaft having a length extending between said proximal handle set and said distal tip, said shaft including:
        an inner layer of polymer material extending the length of the shaft and defining an internal lumen;
        a first wire, extending the length of the shaft, wound about an outside surface of said inner layer of polymer material to form an inner cylindrical braid structure having a series of windings;
        a second wire, extending the length of the shaft, wound to form an outer cylindrical braid structure, said inner cylindrical braid structure being disposed substantially inside of said outer cylindrical braid structure; and
        an intermediate layer of polymer material, extending the length of the shaft, extruded over said first wire, said second wire is wound on an outer surface of said intermediate layer of polymer material, wherein said intermediate layer of polymer material is disposed between said first wire and said second wire, said intermediate layer of polymer material further extending between successive ones of said windings so as to contact opposite facing surfaces of said successive ones of said windings, wherein said first wire, said second wire and said intermediate layer of polymer material are coaxial and each extend between said proximal handle set and said distal tip;
    said first wire having a minor cross-sectional dimension and a major cross-sectional dimension, where said major dimension is greater than said minor dimension; and
    said first wire and second wire and said intermediate layer of polymer material disposed therebetween defining a dual braided body section, wherein a braiding parameter of said inner cylindrical braid structure in said dual braided body section changes along a length of said inner cylindrical braid structure to vary a first mechanical property of said shaft of said catheter apparatus, and a braiding parameter of said outer cylindrical braid structure in said dual braided body section changes along a length of said outer cylindrical braid structure, independently of said braiding parameter of said inner braid structure, to vary a second mechanical property of said shaft of said catheter apparatus, wherein said first mechanical property is different than said second mechanical property.

2. The apparatus of claim 1, wherein said first wire is oriented such that said major dimension is substantially aligned with a longitudinal axis of said inner braid structure.

3. The apparatus of claim 1, wherein said first wire is oriented such that said minor cross-sectional dimension is substantially aligned with a radial axis of said inner cylindrical braid structure.

4. The apparatus of claim 1, wherein an outer polymer layer is disposed at least partially outside of said outer cylindrical braid structure.

5. The apparatus of claim 4, wherein said inner layer, inner cylindrical braid structure, intermediate layer of polymer material, outer cylindrical braid structure and outer layer define an integral laminar shaft.

6. The apparatus of claim 4, wherein said outer cylindrical braid structure and outer layer cooperate to provide said second mechanical property to a longitudinal section of said catheter apparatus, said second mechanical property being torsional rigidity.

7. The apparatus of claim 6, wherein said torsional rigidity is a function of a cross-sectional dimension of said second wire and said braiding parameter of said outer cylindrical braid structure.

8. The apparatus of claim 6, wherein said torsional rigidity is a function of material properties of said outer polymer layer.

9. The apparatus of claim 1, wherein said second wire has a minor cross-sectional dimension and a major cross-sectional dimension, where said major dimension is greater than said minor dimension.

10. The apparatus of claim 1, wherein said inner braid structure and said intermediate layer of polymer material cooperate to provide said first mechanical property to a longitudinal section of said catheter apparatus, said first mechanical property being that said longitudinal section is substantially incompressible in use.

11. The apparatus of claim 10, wherein said first mechanical property is a function of said major cross-sectional dimension of said first wire and said braiding parameter of said inner cylindrical braid structure.

12. The apparatus of claim 10, wherein said first mechanical property is a function of material properties of said intermediate layer of polymer material.

13. The apparatus of claim 1, wherein said first wire has a first relationship of pic rate as a function of length of said dual braided body section and said second wire has a second relationship, different than said first relationship, of pic rate as a function of length of said dual braided body section.

14. The apparatus of claim 1, wherein said first mechanical property is axial rigidity.

15. The apparatus of claim 14, wherein said second mechanical property is torsional rigidity.

16. The apparatus of claim 1, wherein said second mechanical property is torsional rigidity.

17. The apparatus of claim 1, wherein said first wire is a flat wire.

18. The apparatus of claim 17, wherein said second wire is a flat wire.

19. A catheter apparatus, comprising:
a proximal handle set;
a distal tip; and
a shaft having a length extending between said proximal handle set and said distal tip, said shaft including:
   a first layer of polymer material, extending the length of the shaft, defining at least one internal lumen;
   a first wire, extending the length of the shaft, wound to form an inner cylindrical braid structure substantially on an outer surface of said first layer, said inner cylindrical braid structure having a series of windings;
   a second layer of polymer material, extending the length of the shaft, extruded on an outside of said inner cylindrical braid structure wherein said first wire is embedded in said second layer of polymer material, said second layer of polymer material further extending between successive ones of said windings and contacting opposite facing surfaces of said successive ones of said windings; and
   a second wire, extending the length of the shaft, wound to form an outer cylindrical braid structure substantially on an outer surface of said second layer of polymer material, where said second polymer layer material is disposed between said first wire and said second wire;
   said first wire and said second wire with said second layer of polymer material disposed therebetween defining a dual braided shaft, wherein said dual braided shaft extends between said proximal handle set and said distal tip, wherein a braiding parameter of said inner cylindrical braid structure in said dual braided shaft can be changed along a length of said inner braid structure to vary a first mechanical property of said catheter apparatus, and a braiding parameter of said outer cylindrical braid structure in said dual braided shaft can be changed along a length of said outer braid structure, independently of said braiding parameter of said inner cylindrical braid structure, to vary a second mechanical property of said catheter apparatus, wherein said first mechanical property is different than said second mechanical property.

20. The apparatus of claim 19, wherein said first wire is a flat wire having a minor cross-sectional dimension and a major cross-sectional dimension, where said major dimension is greater than said minor dimension.

21. The apparatus of claim 20, wherein said first wire is oriented such that said minor cross-sectional dimension is substantially aligned with a radial axis of said inner cylindrical braid structure.

22. The apparatus of claim 19, wherein said second wire is a flat wire having a minor cross-sectional dimension and a major cross-sectional dimension, where said major dimension is greater than said minor dimension.

23. The apparatus of claim 19, further comprising an outer layer of polymer disposed at least partially outside of said outer cylindrical braid structure.

24. The apparatus of claim 19, wherein said first wire has a first relationship of pic rate as a function of length of said dual braided body section and said second wire has a second relationship, different than said first relationship, of pic rate as a function of length of said dual braided body section.

* * * * *